(12) United States Patent　　(10) Patent No.:　　US 7,243,387 B2
Schindler　　(45) Date of Patent:　　Jul. 17, 2007

(54) POSITIONING AID FOR USE IN PERFORMING A TOMOGRAPHIC FUNCTIONAL EXAMINATION OF THE CERVICAL SPINE

(76) Inventor: Rolf Schindler, Wiesengasse 14, 97424, Schweinfurt (DE)

( * ) Notice: Subject to any disclaimer, the term of this patent is extended or adjusted under 35 U.S.C. 154(b) by 911 days.

(21) Appl. No.: 10/296,837

(22) PCT Filed: Mar. 15, 2001

(86) PCT No.: PCT/DE01/00963

§ 371 (c)(1),
(2), (4) Date: Jul. 21, 2003

(87) PCT Pub. No.: WO01/93764

PCT Pub. Date: Dec. 13, 2001

(65) Prior Publication Data

US 2004/0098803 A1　　May 27, 2004

(30) Foreign Application Priority Data

Jun. 2, 2000　(DE) .......................... 200 09 875 U

(51) Int. Cl.
　*A61B 6/04*　(2006.01)
　*A61G 7/07*　(2006.01)
(52) U.S. Cl. .................. 5/601; 5/615; 5/622
(58) Field of Classification Search ............ 5/601, 5/615, 613, 622, 621, 600, 659, 660; 378/209
See application file for complete search history.

(56) References Cited

U.S. PATENT DOCUMENTS 3,781,928 A * 1/1974 Swallert ................. 5/660

(Continued)

FOREIGN PATENT DOCUMENTS

DE　　3514040 A1 * 10/1986
JP　　06133832 A * 5/1994

OTHER PUBLICATIONS

J. Tacke, et al., "Eine Stufenlose Pneumatische Bewegungsvorrichtung Fur Die Dynamische Mrt Der Halswirbelsaule" Technische Mitteilung, 1999, 171, pp. 249-253, Georg Thieme Verlag Stuttgart, New York.

*Primary Examiner*—Robert G. Santos
(74) *Attorney, Agent, or Firm*—Walter A. Hackler

(57) ABSTRACT

A positioning aid (1) for tomographic functional examinations with a base plate (3) which is connected to a moveable patient trolley and with a shoulder plate at the same height as the thorax, which permits a continuously diagonal positioning of the thorax, at the head-end of the shoulder plate, a swivelling reclining plate (23) is linked to an articulated axle (22a) which runs horizontally in a direction transverse to the z-direction, it being possible to lower the said plate in the direction of the base plate, this being characterised in that the shoulder plate is in the form of a first raising plate (4) which is linked to the base plate facing away from the head, this being swivelled via a horizontal articulated axle (5) and in that a first raising pouch (6) of an elastic material is situated between the base plate and the first raising plate, which when filled with a fluid raises the first raising plate from the base plate from one side, in that when the raising plate raises or lowers, the reclining plate moves with it via the articulated axle, whereby it is movable in a z-direction at the end which faces away from the articulated axle, it preferably being positioned on a support surface (24) in such a way that it is displaceable. This enables the complete range of the physiological scope of the CVC movements of a patient being examined in a tomograph which can be visualised to be defined and reproduced in a manner which is precisely adjustable, amended and fixed. The positioning aid is of a simple mechanical design and enables the patient to be positioned as required in a closed tomograph, in order to enable a functional examination of the CVC to be carried out by continuously adjustable means, whereby a functional examination of the LVC is rendered possible by simply extending the positioning aid with no great technical effort.

20 Claims, 12 Drawing Sheets

U.S. PATENT DOCUMENTS

Figure 1B:
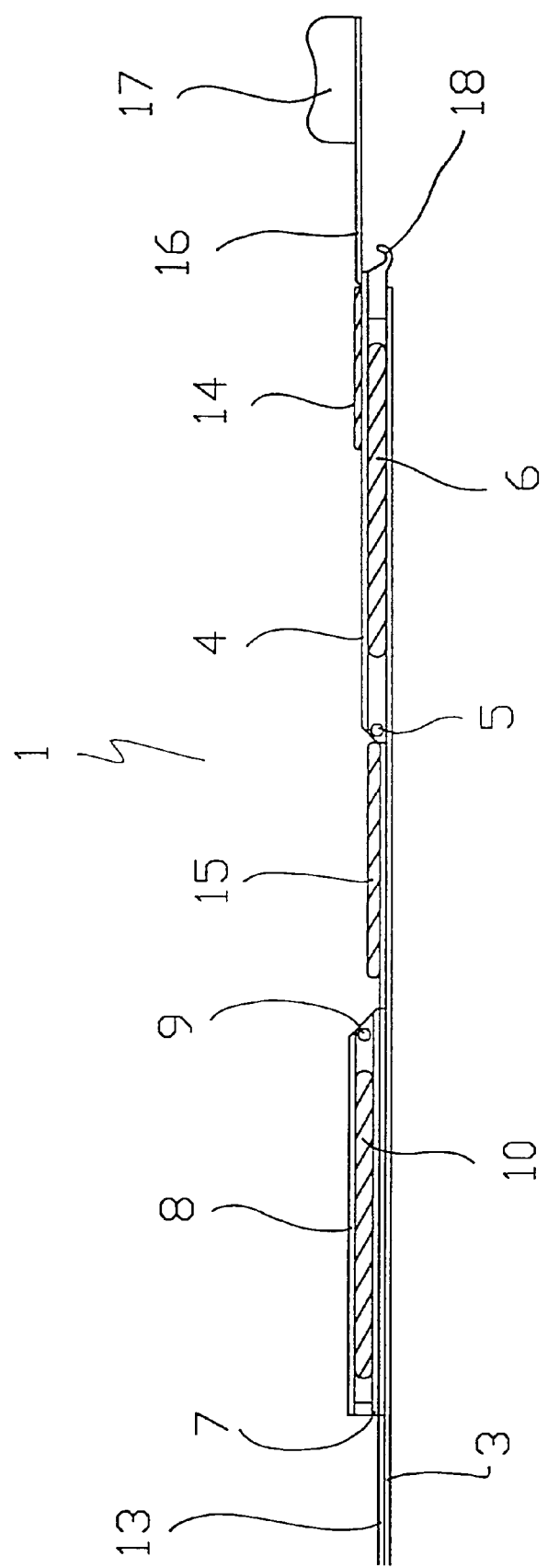

| | | | |
|---|---|---|---|
| 4,099,276 A * | 7/1978 | Hunt et al. | 5/615 |
| 4,349,924 A * | 9/1982 | Zur | 5/618 |
| 5,349,956 A * | 9/1994 | Bonutti | 600/425 |
| 5,416,939 A * | 5/1995 | Maalouli | 5/610 |
| 5,542,423 A * | 8/1996 | Bonutti | 600/415 |
| 5,577,278 A * | 11/1996 | Barker et al. | 5/615 |
| 5,640,958 A * | 6/1997 | Bonutti | 600/415 |
| 5,724,970 A * | 3/1998 | Votruba et al. | 600/415 |
| 5,743,264 A | 4/1998 | Bonutti | |
| 5,772,595 A * | 6/1998 | Votruba et al. | 600/415 |
| 5,806,115 A * | 9/1998 | Brown | 5/615 |
| 5,810,006 A * | 9/1998 | Votruba et al. | 600/415 |
| 5,899,859 A * | 5/1999 | Votruba et al. | 600/415 |
| 6,012,186 A * | 1/2000 | Soltani et al. | 5/614 |
| 6,684,095 B1 * | 1/2004 | Bonutti | 600/415 |
| 6,882,877 B2 * | 4/2005 | Bonutti | 600/410 |
| 2004/0098803 A1 * | 5/2004 | Schindler | 5/601 |

* cited by examiner

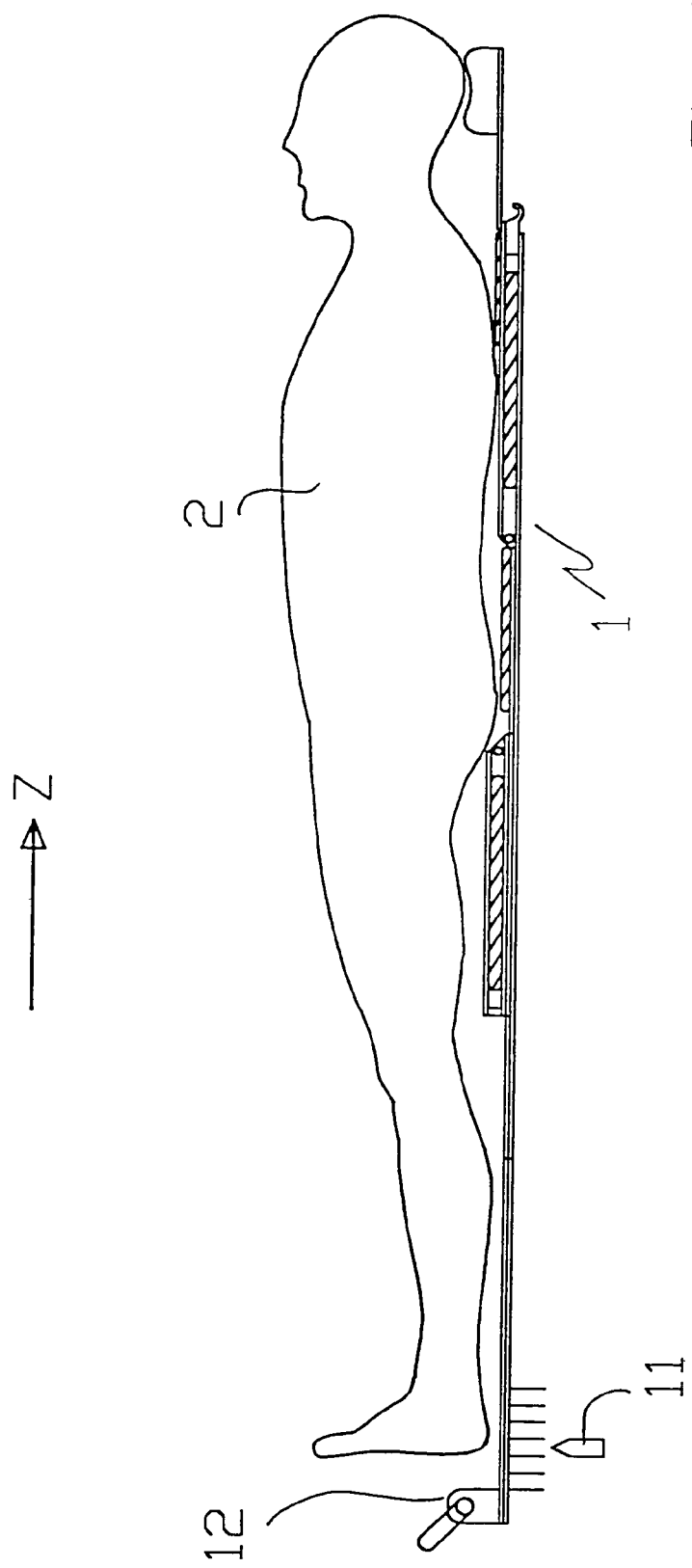

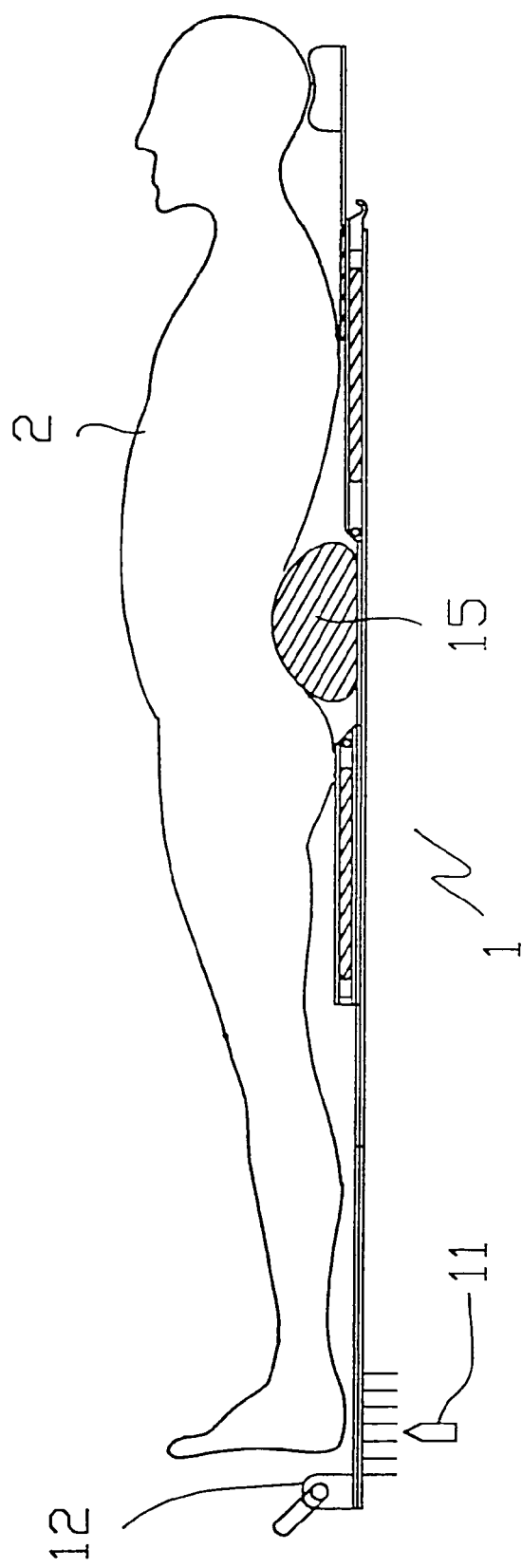

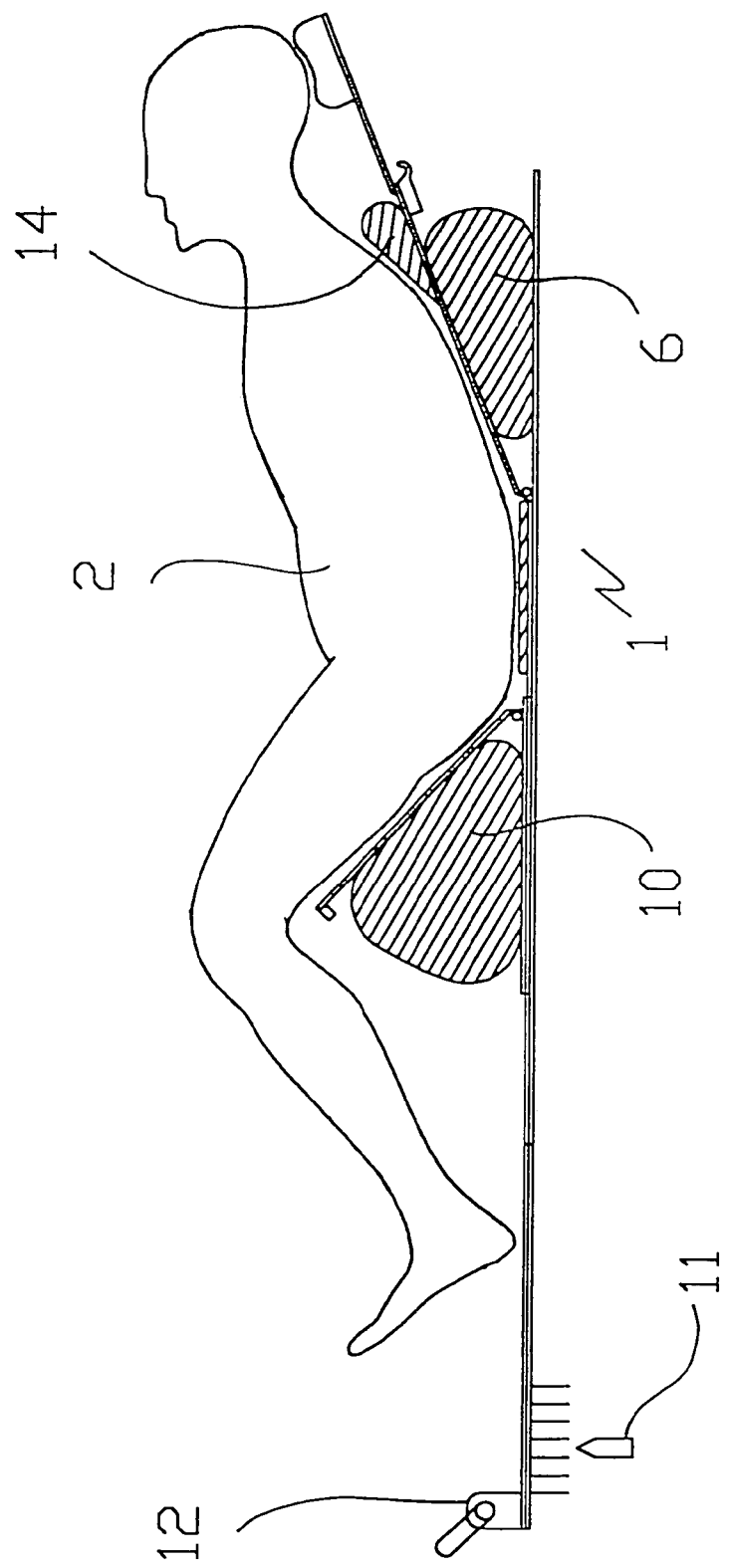

POSITIONING AID FOR USE IN PERFORMING A TOMOGRAPHIC FUNCTIONAL EXAMINATION OF THE CERVICAL SPINE

The invention concerns a positioning aid for the tomographic functional examination of vertebrates, especially humans, with a base plate which extends along a z-direction parallel to the tomograph axis, the said plate being preferably interlocked with a mobile trolley, whereby a shoulder-plate is fitted to the base plate, in the same position as the thorax of the patient who is being examined, enabling the position thorax area of the patient being examined to be continuously raised in the direction of the head when seen in comparison with the position of the base plate, a swivelling reclining plate being linked to an articulated axle which runs horizontally in a direction transverse to the z-direction horizontal being jointed via an articulated axle, it being possible to lower the said plate in the direction of the base plate.

Such a positioning aid for the tomographic functional examination of the cervical vertebral column has already been described in the articles from J. Tacke et all. "Eine stufenlose pneumatische Bewegungsvorrichtung für die dynamische MRT der Halswirbelsäule" [A Continuously Variable Pneumatic Moving Device for a Dynamic MRT of the Cervical vertebral column" in the magazine, Fortschr Röntgenstr 171 (1999) 249–253.

Examinations of the vertebral column make out an extremely large part of the daily tomography practice, especially the magnetic resonance tomography (=MRT), the reason being that the diagnostic potential is much better than with the conventional (X-Ray) process due to it being possible to differentiate between the different tissue types. However, in principle, examinations such as these can also be carried out with computer tomography (=CT).

The development of new pulse sequences in the MRT enables an high-resolution delineated imaging of the vertebral canal with its liquor, bones, intervertebral disks, ligaments or even vessels against each other and the surrounding tissue without the use of a contrast agent as necessary, depending on the diagnostic objective.

In addition, modern digital image processing together with fast computers are also able to compile the individual data records to form a complete anatomical image and also provide 3-D imaging—for the planning of operations, for example. Additional scanning planes can also be subsequently imaged without any additional examinations being necessary.

For the radiologists, one of the greatest disadvantages of the MR-imaging in the vertebral column diagnostic is that it is practically speaking, still not possible to effectively carry out tests in different functional positions (as is normally the case with the conventional myelography).

Due to the relative confinement of the magnets used in the diagnostic, many radiologists believe that the achievable space for movement does not suffice for the obtaining of additional diagnostic findings. In connection with this, open MR-units have been used on occasions. However, the majority of the radiologists do not have access to such units. It is also the case that high-resolution images can only be produced to a certain extent due to the low magnetic field intensity.

The literature from the past has often described experiments which were directed at functional positioning with more or less experimental positioning aids. These experiments have at least proven that certain functional positions are possible and also suffice to clarify special objectives which were in the past not accessible for the MRT and which were only difficult to clarify, if this was indeed at all possible.

However, as far as the routine diagnostic is concerned, all of these positioning aids are of little use (assuming that they are even commercially available) as the many and diverse movement possibilities of the complete vertebral column make it necessary to employ a large number of individual devices which must be fitted or removed for other movements. In addition, this renders combined movements almost impossible. Purely mechanical models must also often be manually adjusted by the examining person which could result in a situation whereby the patient trolley must even be removed from the tomograph.

In the practise, this results in the examination durations being too long, up to now, the functional MR-examinations of the vertebral column are more or less left to the research scientists.

In addition to the positioning aid from J. Tacke et al. described at the beginning, such an aid also exists as shown in a company brochure from 1999, issued by the company ulrich Medizintechnik, Buchbrunnenweg 12, D-89081 Ulm, the MR-positioning aid being offered here being the model XD 8001, this serving the imaging of the kinetic mechanism of the cervical vertebral column (=CVC). This cannot be used to examine the functions of the lumbar vertebral column. The relatively complicated mechanical construction can only be manually adjusted so that every time the patient has to be re-positioned or the position adapted, the patient must be removed from the tomograph together with the positioning aid. In addition, this known MR-positioning aid can only be used for between four and seven discrete patient positions, but not a continuous positioning in any given intermediate positions.

Contrary to this, the positioning aid for dynamic CVC examinations from J. Tacke et al. mentioned at the beginning permit a continuously variable pneumatic movement, whereby any intermediate positions are continuously possible at the same position as the patient's head within the scope of MR-tomograph examinations. During the CVC examinations which can be carried out using this positioning aid, the patient's shoulder is rigidly positioned, whereby the upper part of the body is already positioned in an upwards diagonal position. This results in a heavily restricted scope for movement in the inclination area of the CVC due to the inclination position only being achieved from a fixed reclining position of the CVC. A normal horizontal positioning of the patient is absolutely not possible when using the known positioning aid. Due to the thorax positioning of the patient right from the beginning, the inclination examination of the CVC results in a non-physiological positioning and therefore an unnatural, often uncomfortable or even painful pressure being applied to the bend of the patient's neck.

A completely different design of positioning aids is that described in the corporate brochure "Joint Motion Device Operator Manual Siemens" from the company Chamco Inc. Cocoa, Fla., U.S.A., 1996. Among others, joints can be examined with this device, hip joint examinations also being possible, whereby the devices are normally designed for open MR-tomographs with access possibilities from outside the tomograph. Although it is the case that some of the described devices are supposed to be compatible with closed high-field magnet systems, their mechanically and hydraulically-driven design requires quite a lot of space and they are very complex. Differentiated movement possibilities for the adjustment of the function positions of the CVC are not planned. This means that two devices are especially required when carrying-out CVC LVC examinations. A defined raising of a patient's shoulder and/or pelvic area when they are laying on their back is not possible.

In comparison with this, the task of the invention in question is the presentation of a positioning aid for a tomograph examination of the CVC with the properties stated at the beginning, with which it is possible to visualise the full range of the physiologically visual scope of the CVC movements of the patient being examined in the tomograph, the said device being continuously variable and precisely adjustable, correctable and fixable from the outside, whereby the positioning aid should be so mechanically designed and permit a positioning enabling all of the functional closed tomograph examinations of the CVC to be carried out in that the position of the patient can be continuously adjusted, whereby it should be possible to carry out an examination of the LVC by means of a simple extension of the positioning aid with a minimum of technical difficulties.

With the invention, this task was solved by surprisingly easy ways and means in that the shoulder plate is firstly designed in the form of a raising plate, the end of which is linked to the base plate facing away from the head, this being swivelled via an articulated axle which is parallel to the articulated axle of the reclining plate, and in that a first raising pouch of an elastic material is situated between the base plate and the raising plate, which when filled with a fluid raises the first plate from the raising plate from one side, in that when the raising plate raises or lowers, the reclining plate moves with it via the articulated axle, whereby it is movable in a z-direction at the end which faces away from the articulated axle, it preferably being positioned on a support surface in such a way that it is displaceable.

This means that all of the physiologically possible scope of the reclining in the CVC area can be visualised continuously variably easily and with a minimum space requirement with the simplest mechanical means. With the assistance of the fluid-driven first raising plate, any continuously raised positions of the vertebral column is possible commencing from the horizontal position and moving diagonally upwards towards the shoulder.

The remote-controlled movement of the raising plate by means of a fluid filling of or a fluid extraction from the corresponding raising pouch is preferably carried out using compressed air. In principle, it is also conceivable that a hydraulic drive can be used instead of a pneumatic one. In all cases, the fluidic drive guarantees continuous and smooth movement of the positioning aid as is necessary for the positioning of the patient.

The movement of the devices can be remotely controlled from an operating console situated outside the tomograph. For example, the movement in the MR-tomograph can be produced by utilising faster sequences in the projection direction ("imaging") of the movement process because the fluidic drive also enables extremely slow movements to be made. In addition, the corresponding movement can be halted at any given position, for high-resolution sequences, for example.

It is especially the case that reproducible adjustments can be mad with the positioning aid before an operation and for post-operative control examinations and quality assurance.

The invented positioning aid can especially be used to realise all of the relevant movements and their combinations within the physiologically required scope during MR-examinations.

Due to the low height of the invented positioning aid which results from the simple mechanical design, it is possible to carry out examinations in the normal position with almost no loss of quality. The device can also remain in the tomograph for the carrying out of many other examinations (possibly except for examinations of the head or mammographs).

With an especially advantageous form of the design of the invented positioning aid, it is intended that an inclination rocker be fitted at the same height as the examined patient's head, the said rocker having a recess in which the reclining plate is retained in the normal position, the inclination rocker having two swivel fixed pivot brackets positioned laterally to the left and right of the head end, which can be swivelled around a joint horizontal vertical swivelling axis, which can be swivelled in the z-direction, whereby the swivelling axis is positioned with vertical clearance from the base plate, it also being intended that a raising pouch which can be filled with a fluid and preferably inflated, be positioned between the base plate and the inclination rocker. In this case, every inclination movement of the patient's head is mainly possible around the physiological axis of rotation with the assistance of the invented positioning aid.

Preferably, the clearance between the swivelling axis of the inclination rocker and the base plate is such that it is possible to rotate the head of the patient being examined around its physiological axis of rotation. This enables the movements to be optimally adapted to the individual physiological situation of the vertebrates, especially human patients.

An additional advantageous design of the aforementioned design is that the linking of the reclining plate is so designed that when the inclination rocker is activated, the reclining plate is released from the first raising plate. This results in the inclination rocker automatically taking the reclining plate with it during the inclination movement.

This can especially be achieved in a simple and inexpensive manner in that the coupling of the reclining plate to the first raising plate is realised in that the reclining plate is linked by means of the pins in the reclining plate, in that it hooks into a hook-shaped recess in the first raising plate which should preferably face upwards. This provides a mechanical solution which is especially functionally secure.

An additional advantageous design is that the invented device is characterised in that a lateral flexion shell is positioned in the area of the head of the patient being examined, this being connected to the reclining plate via a slide ring in such a manner that it can be moved along a vertical axis, whereby the vertical axis normally corresponds with the physiological axis of rotation of the head of the patient being examined. This results in it being possible to carry out a defined lateral movement of the head to be carried out independently from other movements or in combination with inclination and/or reclining movements, it also being possible to fix it in a given intermediate position.

The design can also be advantageously equipped in that a length compensation shell is positioned in the lateral flexion shell in the normal position which can be moved linear in a direction parallel to the z-direction. This provides a length compensation of the various neck lengths of various patients together with a fine adaptation to the physiological movement of the head when inclining and/or reclining.

An additional improvement is that a rotation shell is situated in the length compensation shell which can be rotated around a horizontal axis which is situated parallel to the z-direction in the normal position, it also being able to fix it in position. This enables the head to be rotated in combination with other movement possibilities.

The lateral flexion shell can also be hollow in order to enable other functional units to be installed, whereby the dimensions of the device as a whole is to be kept as compact as possible. The first raising plate, the other raising plate and any other moving or fixed parts of the invented device can also be hollow. These cavities especially enable electrical devices to be installed in connection with the tomographic examinations to be carried out, with a minimum space requirement and so that they are close to the patient being examined.

If the tomograph used is a magnetic resonance unit, one or more surface coils can be installed in the cavity of the lateral flexion shell.

In other design examples, the lower half of a surface coil system can be installed in the cavity, the corresponding top half of the surface coil system being situated outside the cavity.

An especially preferred design of the invented positioning aid is one whereby an additional raiseable raising plate is situated at the foot, the said plate being linked to a moving slide which moves in a longitudinal linear direction, the articulated axle of the plate running parallel to the articulated axle of the first raising plate, whereby an additional raising pouch filled with a fluid and preferably inflatable, is situated between the slide and the additional raising plate, a device for the detection of the position of the slide in relation to the first raising plate is envisaged, it being possible to lock the slide in a determinable position in relation to the first raising plate.

With this design, it is possible to use the invented positioning aid for LVC examinations by adding simple technical measures.

In addition, when carrying out normal examinations of the LVC, the patient does not need to be re-positioned or moved out of the unit.

The vertebral column in the lumbar area can also be raised diagonally upwards by means of the additional raising plate at the foot end. With the addition of a movable slide which can be positioned on the first raising plate instead of the additional raising plate, a relative positioning between the two raising plates in the longitudinal direction of the patient is possible so that any number of adjustments can be made in accordance with the size of the patient.

A special preference is an advancement of this design, in which a shoulder pillow is positioned on the first raising plate for an additional raising of the upper part of the shoulder of the patient being examined. Such a shoulder pillow enables the kyphosis position to be heavily improved. This also enables a slight kyphosis position of the thoracic vertebral column to be provided.

In order to enable a remote-controlled adaptation to be provided, the shoulder pillow used with the advancement of this design can be filled with a fluid, preferentially inflatable.

Especially advantageous is an advancement, in which the shoulder pillow is mainly wedge-shaped in the longitudinal section at a vertical level included in the z-axis, whereby the point of the wedge points away from the head of the device. This ensures that the thorax does not raise off the raising plate when the shoulder pillow is raised.

In a preferred advancement of the design of the invented positioning aid with the possibility of examining the LVC, a lordosis pillow is situated between the first and additional raising plate, preferably on the base plate. This enable a lordosis position of the patient to be mechanically provided with very simple methods.

An advantageous design is one whereby the lordosis pillow can be refilled with a fluid, preferably inflatable, enabling a remote-controlled, continuous and smooth adjustment to be made.

An additional advantageous advancement is that the lordosis pillow can be moved in the longitudinal direction of the base plate. This provided more room for movement when adapting the positioning aid to the individual body length of the patient being examined.

In addition, the lordosis pillow can be provided with a concave upper surface transverse to the z-direction, this enabling the patient to be positioned in a stable manner. This especially results in the patient being prevented from rolling-away to one side.

An additional preference is a design of the invented positioning aid, whereby an extension plate is rigidly positioned at the head-end of the first raising plate in such a way that it can be removed, the said extension plate supporting a head pillowing for the support of the head of the patient being examined. This is necessary as a lowering of the head results in a reclining of the CVC, the resulting stretching of the ligaments and muscles opposing the inclination of the LVC. However, the extension plate effectively prevents the LVC from reclining, thereby providing a physiological lordosis positioning of the LVC of the patient being examined, without pain and tension.

An additional preferred design of the invented positioning aid is characterised in that a pelvic pillow is positioned at the same height of the pelvis of the patient being examined, to the side of the centre-axis of the base plate, and that a deflecting device is fitted to the foot end of the patient being examined on the same side at a distance from the centre-axis, the said device being preferably cushioned, it especially being in the form of a deflecting rod for the deflecting of the feet of the patient being examined from the longitudinal direction of the base plate. This enables a defined provision of the lateral flexion of the LVC to be provided with simple mechanical means.

In an advanced version, it should be possible to refill the pelvic pillow with fluid, preferably inflatable, in order to guarantee a smooth remote-controlling of the position adjustment and the making of the adaptations which are necessary due to the patient's girth.

An additional advantageous advancement is that the padding of the deflection device is filled with a fluid, preferably inflatable, which enables a remote-controlled adjustment to be carried out.

What is especially preferred is an advancement of the design of the invented positioning aid with the possibility of examining the LVC, in that the tomograph has a display for the optical visualisation of the position value determined by the device for the position of the slide relative to the first raising plate. The operating console of the tomograph would be particularly suited to this task. This means that the adjustment of the required examination position can be externally monitored.

An improvement of this advancement which is especially advantageous is that the device for the detection of the relative position of the slide includes a signal transmitting sensor which especially transmits a magnetic resonance signal. This guarantees an extremely exact position control, especially during imaging MR examinations.

A special preference is a design of the invented positioning aid, whereby the moving of the slide moving of the slide for the raising of the first raising plate and all filling and emptying actions with regard to the raising pouches or other elastic or non-elastic moveable hollow parts can be activated outside the tomograph. This enables a remote-control adjustment, change, variation, subsequent correction or fixing of every examining position required to be adopted without the patient having to be removed from the tomograph.

In order to avoid disturbances of the imaging components of the tomograph, an additional preferred design is envisaged, whereby all actuators, drive and control units for the invented device are situated outside the tomograph, preferably in a separate room.

Finally, what is especially advantageous is a design whereby all of the actuator units can be actively stopped by the patient being examined. Due to the possibility of the active cooperation of the patient, no extra space is required for corrective actions by the operating personnel. In addition, the comfort of the patient can also be taken into account, it especially being the case that the suffering of pain by the patient resulting from an overstretching in a certain position is avoided.

Additional advantages of the invention are those arising from the description and the drawing. It is also the case that the characteristic features stated above and those additionally stated can either be employed separately or in any combination whatsoever. The designs described and depicted here cannot be seen as being a conclusive listing, on the contrary, they have an exemplary character for the description of the invention.

The invention is depicted in the drawing and is explained in more detail on the basis of the design examples. It depicts:

FIG. 1a a diagrammatic vertical section of a design of the invented positioning aid for CVC and LVC examinations with the patient lying on the same in the normal horizontal position;

FIG. 1b enlarged detail of the positioning aid depicted in FIG. 1a

Figure 2B:
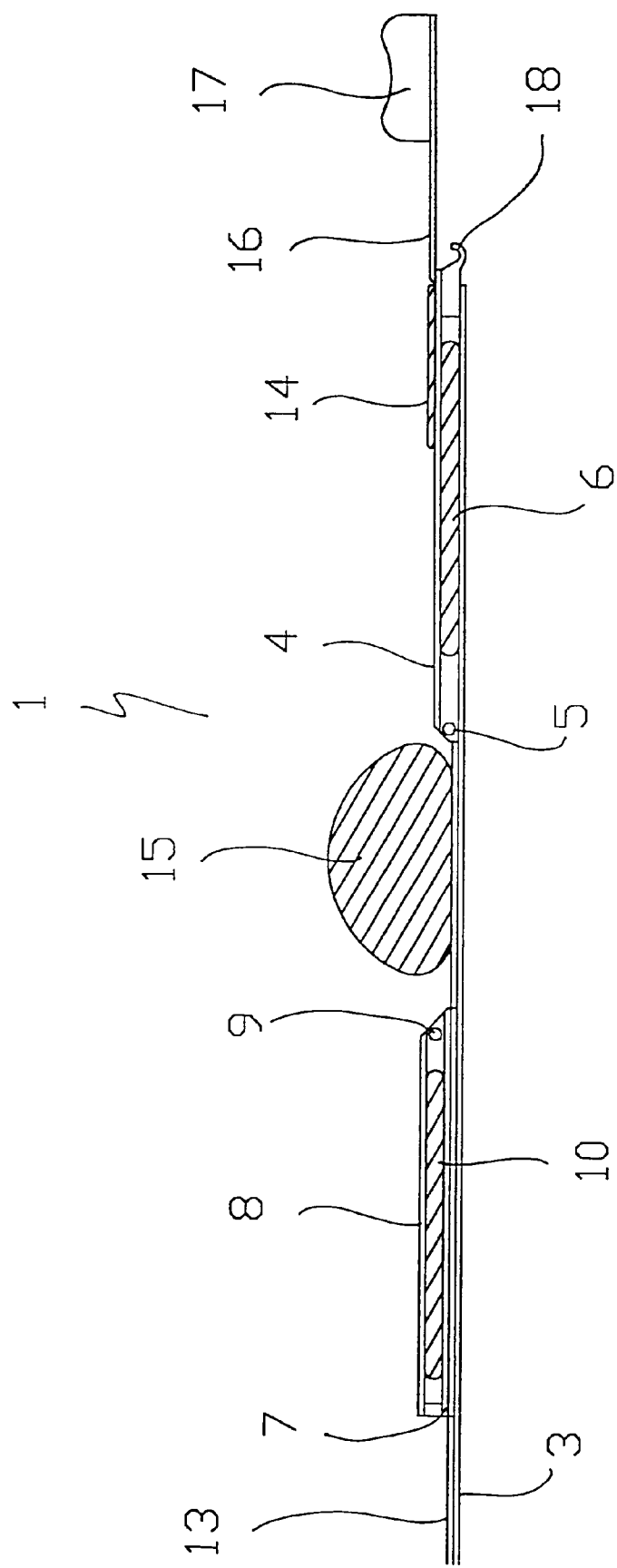

FIG. 2a as FIG. 1a, but with inflated lordosis pillow in the horizontal position;

FIG. 2b enlarged detail of the device depicted in FIG. 2a

Figure 3B:
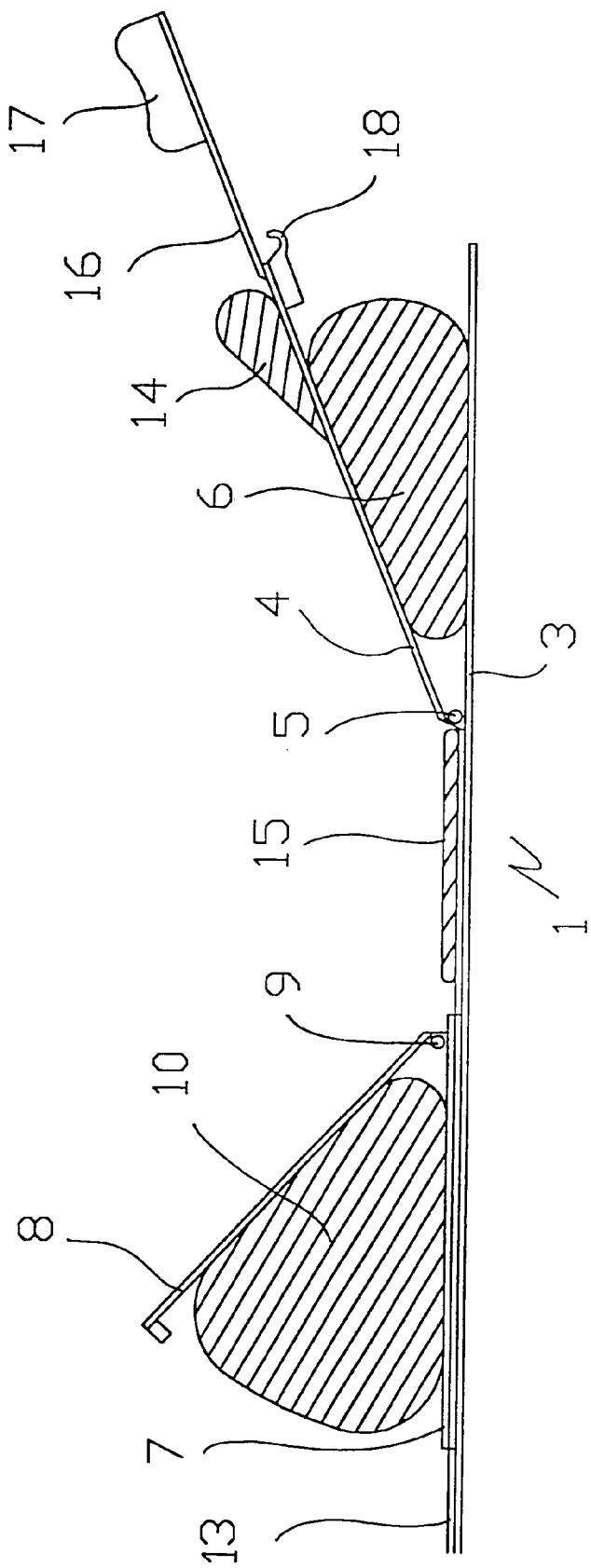

FIG. 3a as FIG. 1a, but in the kyphosis position with inflated first and additional raising pouch together with an inflated shoulder pillow;

FIG. 3b enlarged detail of the device depicted in FIG. 3a

Figure 4:
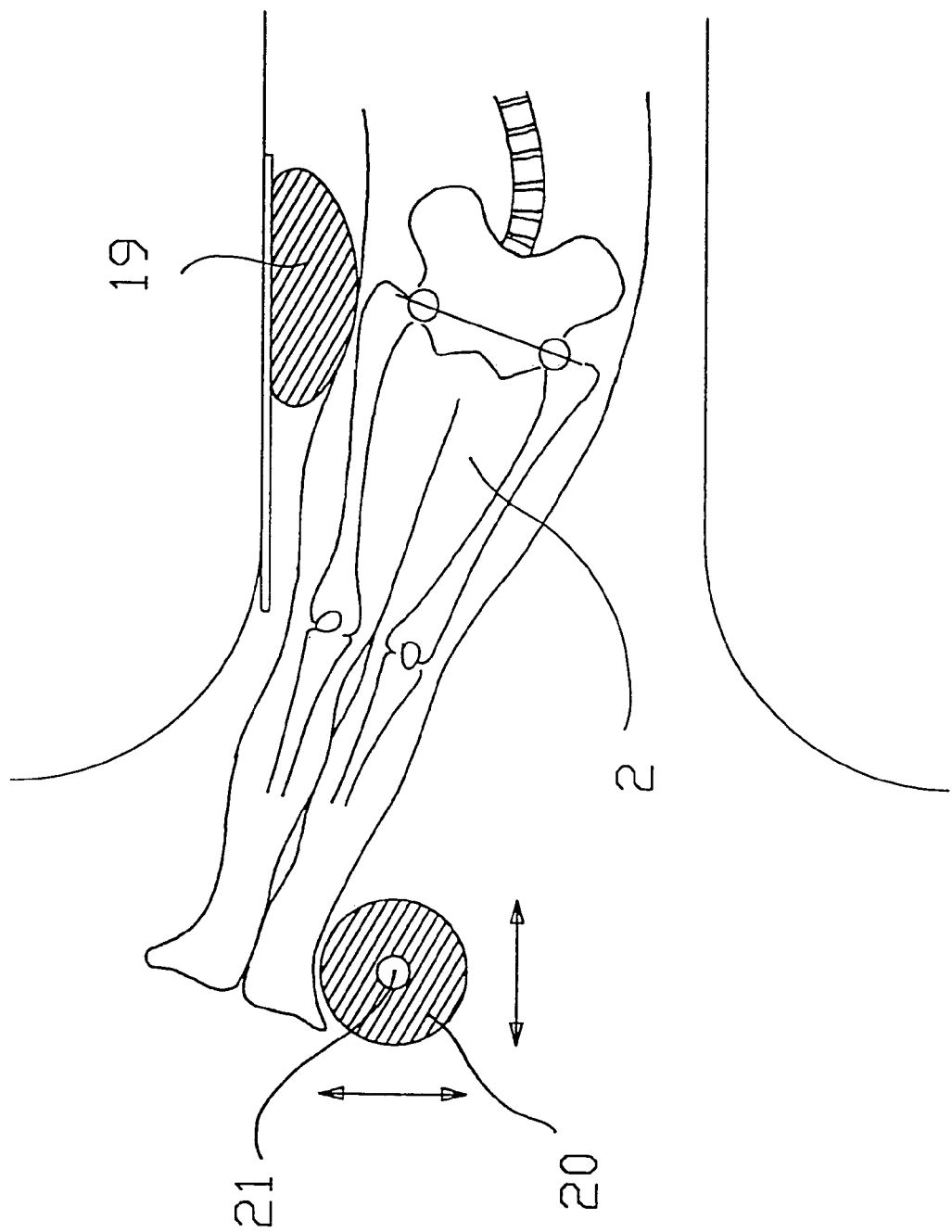
Figure 5:
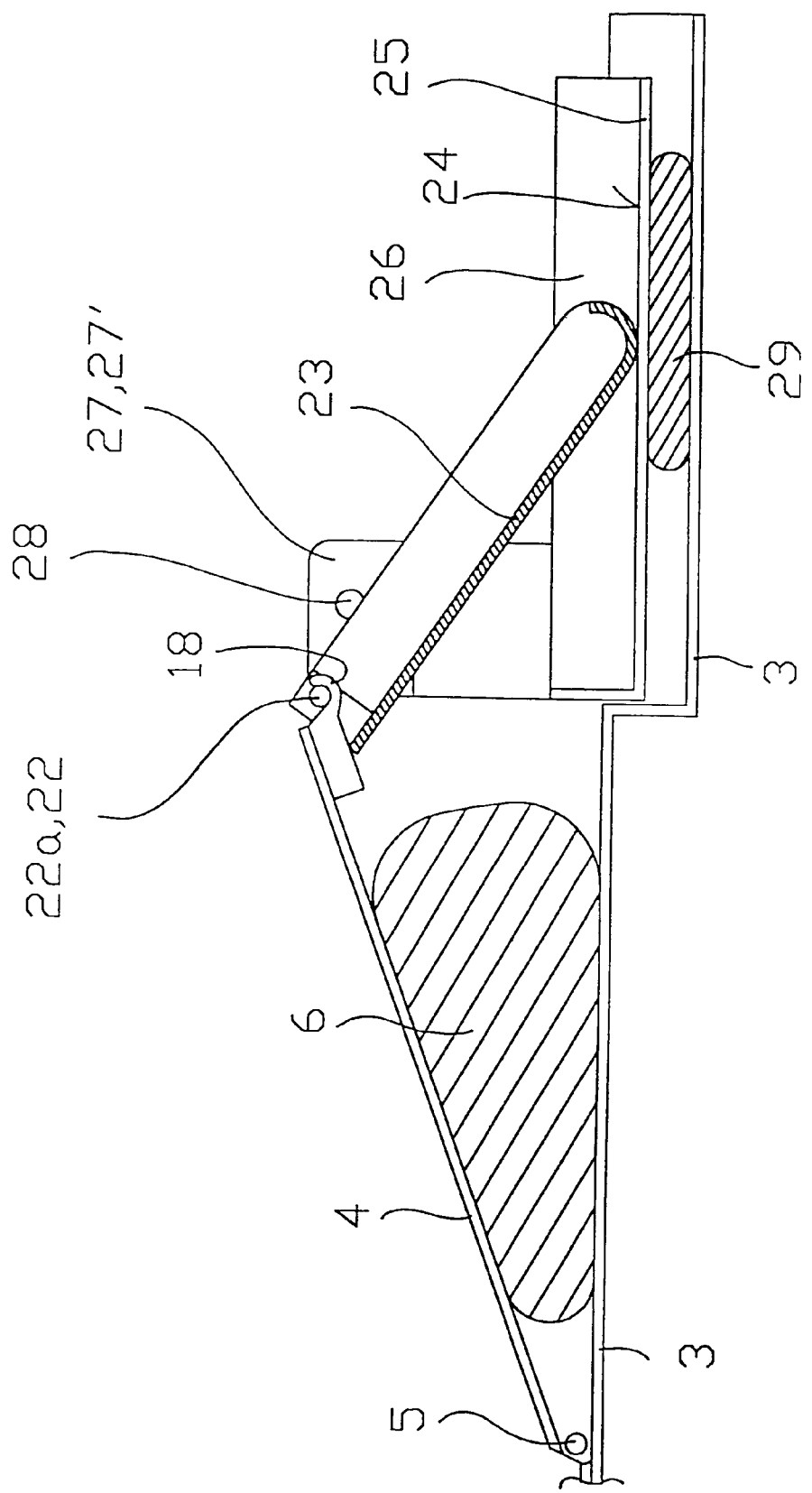
Figure 6:
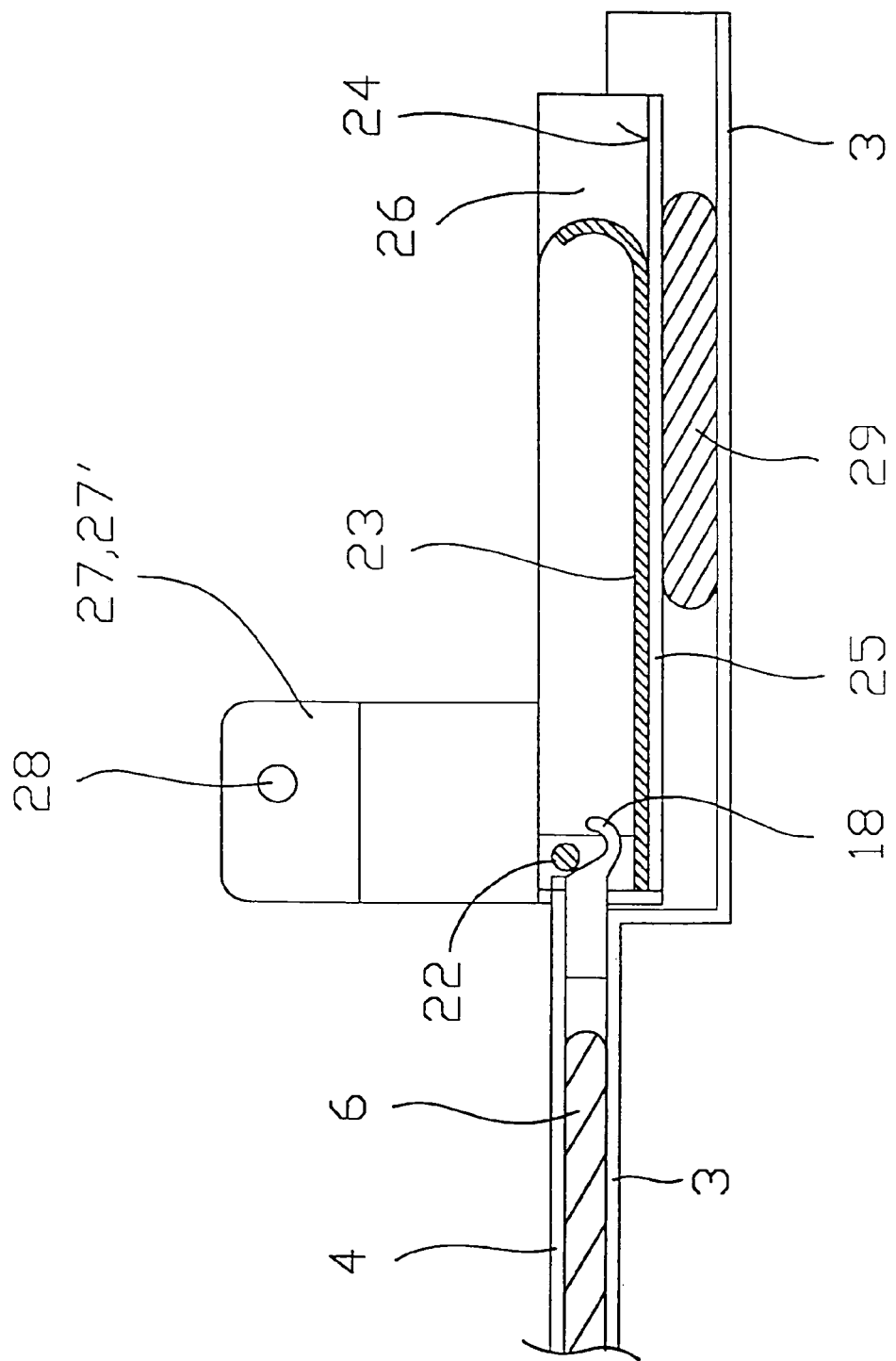
Figure 7:
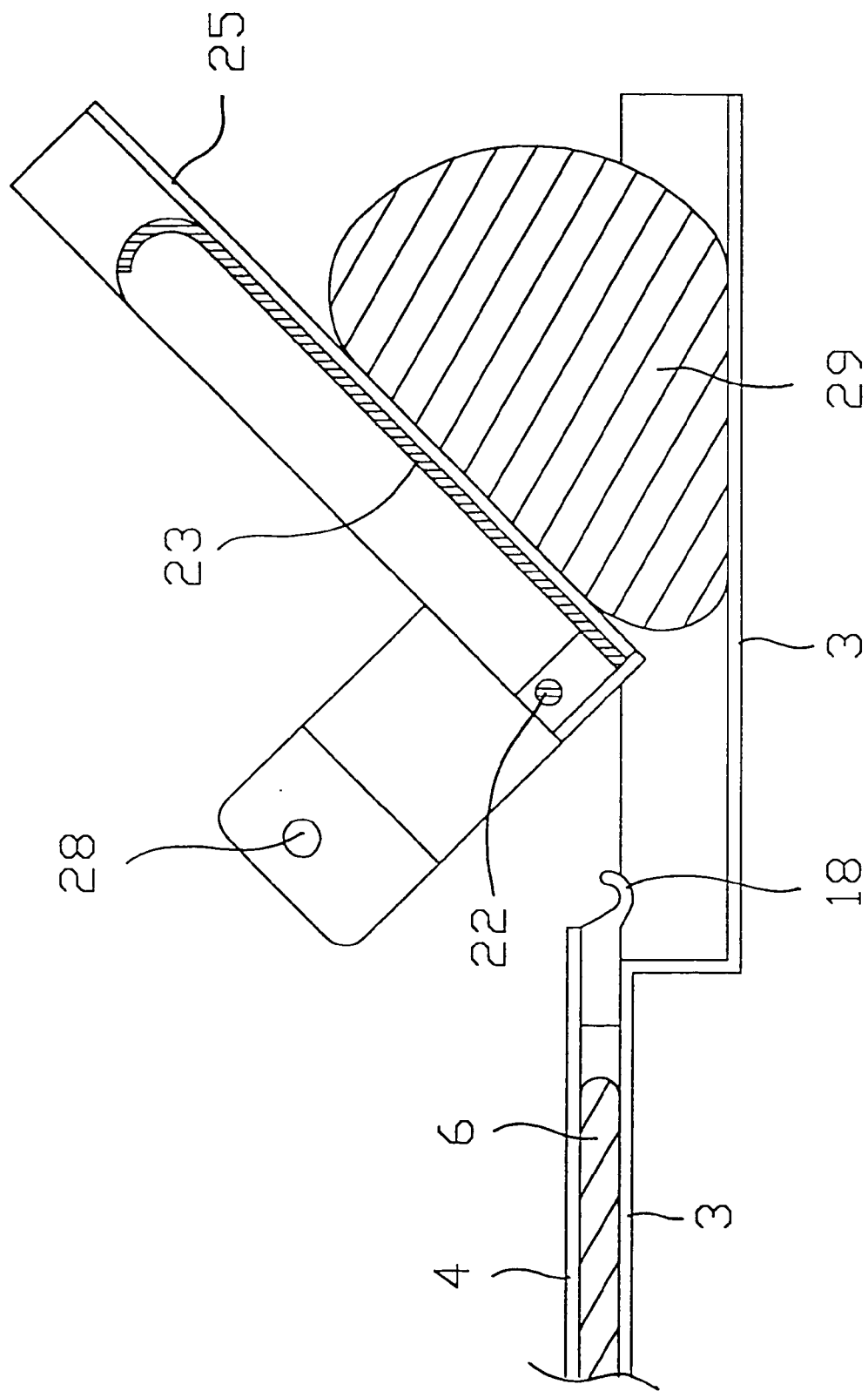
Figure 8:
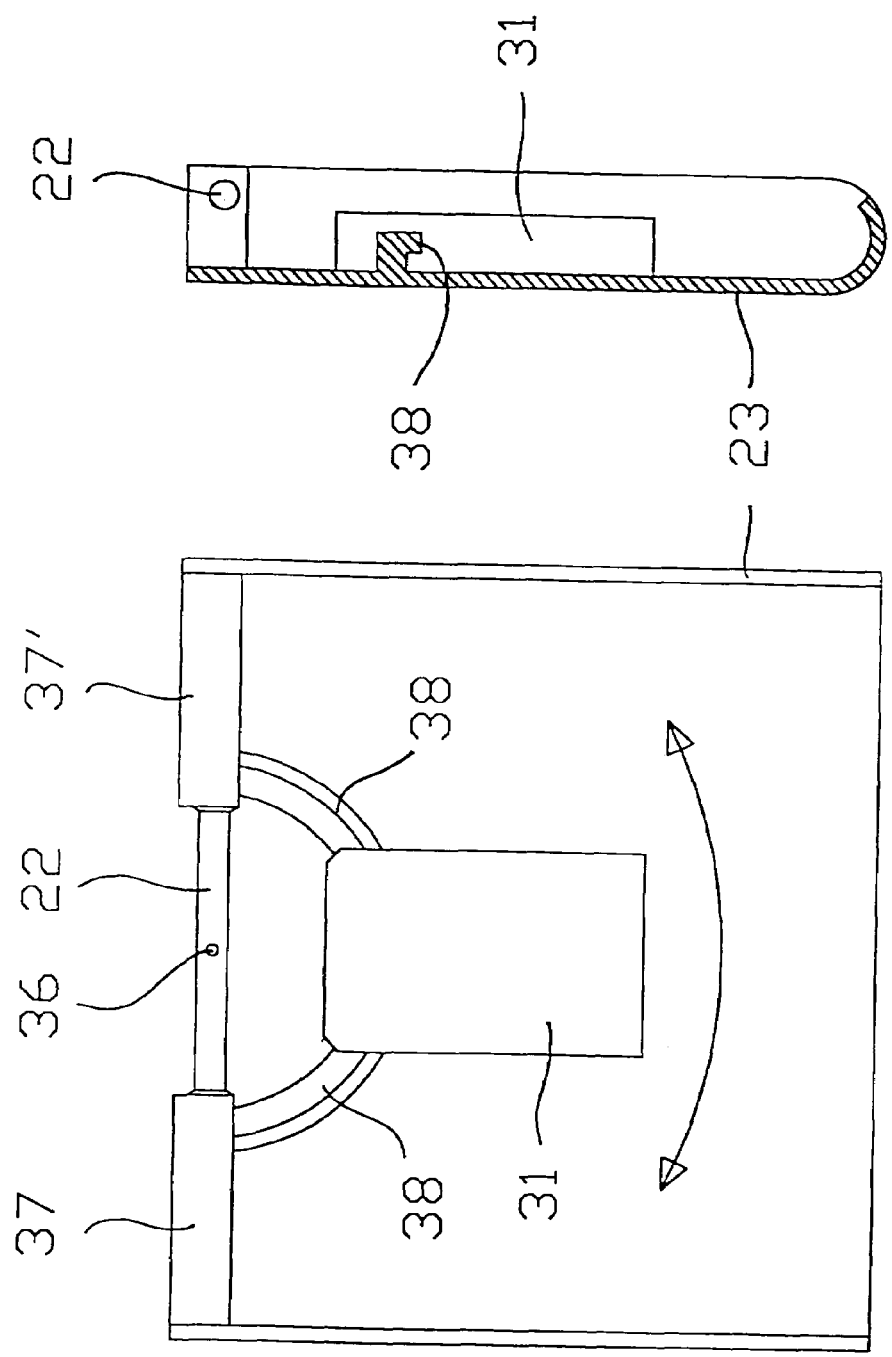
Figure 9:
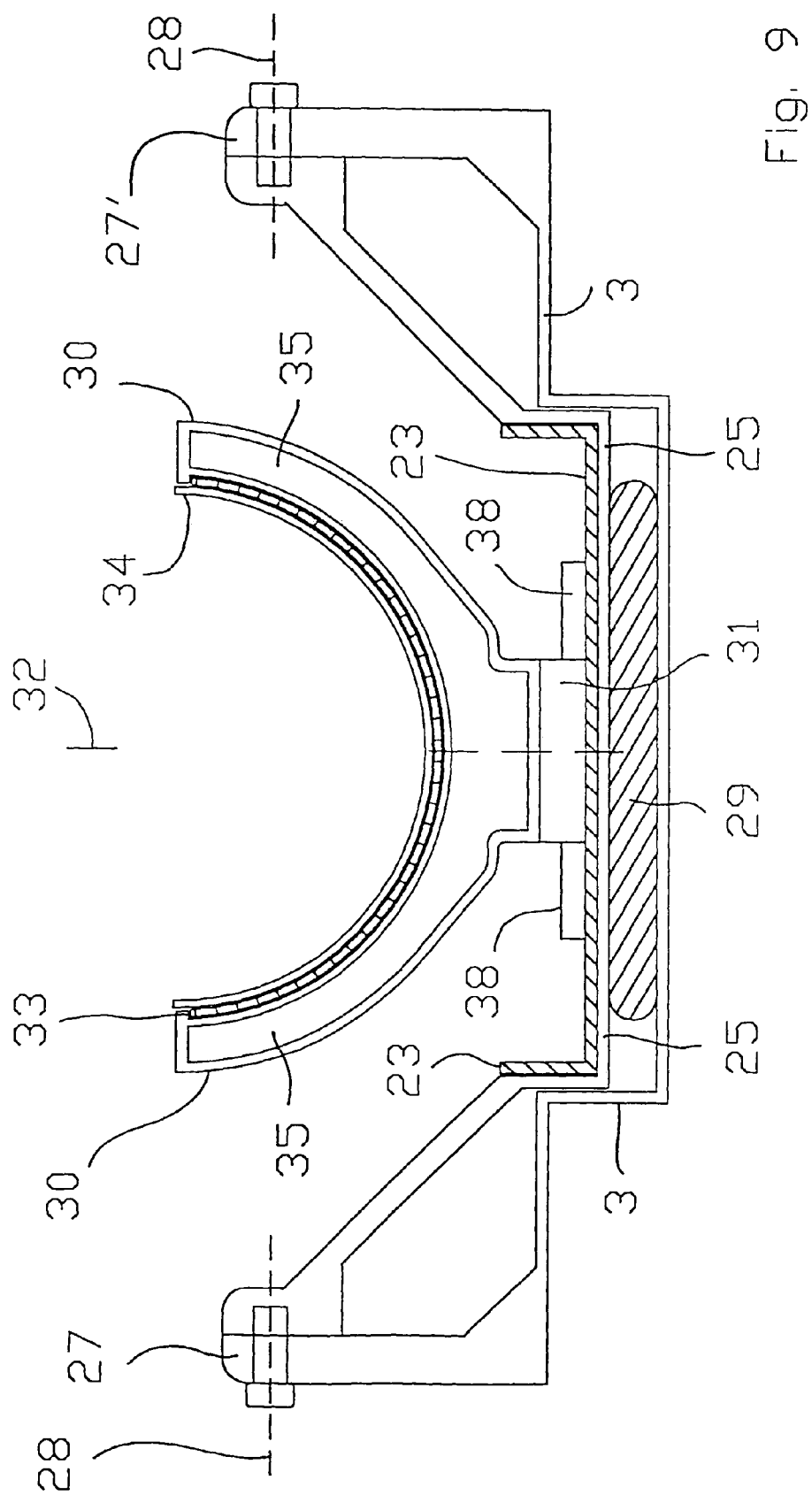

FIG. 4 a diagrammatic horizontal section of a design of the invented positioning aid with a pelvic pillow and a deflecting device for the creation of a lateral flexion position;

FIG. 5 a diagrammatic vertical section of the head-end of the invented positioning-aid with a reclining plate and an inclination rocker in the reclining position of the reclining plate in the raising position of the shoulder plate;

FIG. 6 enlarged detail of the section shown in FIG. 5 in the horizontal normal position of the reclining plate;

FIG. 7 as FIG. 6, but with the inclination rocker situated in the raised inclining position of the CVC;

FIG. 8a a diagrammatic horizontal projection of the reclining plate with a slide ring for a lateral flexion shell from above;

FIG. 8b a vertical section of the centre plane of the reclining plate depicted in FIG. 8a parallel to the z-direction; and FIG. 9 a vertical section on a plane vertical to the z-axis, which retains the jointed axle of the inclination rocker and the vertical axis of rotation of the slide ring supporting the lateral flexion shell.

In the diagrammatic section shown in FIG. 1a, one recognises a design of the invented positioning aid 1 for CVC and LVC examinations in a horizontally extended normal position with a patient 2 lying on it. For reasons of clarity, the special design for CVC examinations is not depicted in FIGS. 1a–4, this is only be the case as from FIG. 5. However, it speaks for itself that the CVC component is fundamental for the invention in question.

In FIG. 1b, the positioning aid 1 depicted in FIG. 1a is shown in a diagrammatic section without patient 2. A shoulder pillow in the form of a raising plate 4 on a base plate 3 extending in a longitudinal z-direction is jointed in a direction transverse to the z-direction which is articulated at its end facing away from the head. A first raising pouch 6 of an elastic material is situated between the base plate 3 and the first raising plate 4, which when filled with a fluid, the first raising plate 4 is able to be raised off the base plate 3 from one side. Furthermore, a raising plate 8 which can be raised from one side is linked to a moveable slide 7 which can be linearly positioned along a guide 13 in a z-direction on a base plate 3 which is intimated diagrammatically, the articulated axle of the said raising plate 8 being positioned parallel to the articulate axle 5 of the first raising plate 4, whereby an additional raising pouch 10 is situated between the slide 7 and the additional raising plate 8, is also being possible to increase the volume of the said pouch, in that it can be filled with a fluid or especially inflated with air, this resulting in a one-sided raising if the raising plate 8 from the slide 7.

As diagrammatically shown in FIG. 1a, a device 11 for the detection of the position of the slide 7 in relation to the raising plate 4 is positioned at the foot-end of the positioning aid 1. The slide 7 can then be locked in position by means of a locking device 12 which is also only diagrammatically intimated.

In addition, a shoulder pillow 14 is shown in FIG. 1b, it being positioned on the first raising plate, this serving to support the shoulder of the patient 2 being examined. As with the raising pouches 6, 10, the shoulder pillow 14 can also be filled with a fluid, but preferably inflated.

Furthermore, a lordosis pillow 15 which can also be filled with a fluid is situated between the first raising plate 4 and the additional raising plate 8, which can be moved in the longitudinal direction of the base plate 3, with a concave surface in the direction of the z-direction when inflated.

An extension plate 16 is rigidly positioned at the head-end of the first raising plate 4 in such a way that it can be removed, the said extension plate supporting a head pillow 17 for the support of the head of the patient being examined 2 for purely LVC examinations. Should it be necessary to carry out CVC or combined CVC/LVC examinations, this is to be mounted on raising plate 4 as shown in FIGS. 5–9.

On the underside of the first raising plate 4, a hook-shaped recess 18 can be discerned in FIG. 1b, this being rigidly linked to the first raising plate 4, the function being explained in more detail below.

FIGS. 2a and 2b each depict the horizontal position with the lordosis pillow 15 in an inflated condition or when filled with a fluid respectively. The raising pouches 6 and 10 being emptied in this position, so that the first raising plate 4 and the additional raising plate 8 are positioned in a horizontal flat position. This makes it possible to bring the patient 2 into a position with a complete kyphosis. The side rolling-away of the patient 2 off the lordosis pillow 15 is on the one side prevented by the aforementioned concave upper surface of the lordosis pillow 15, which is not discernible from the Figure. On the other hand, it is normally the case that a rolling-away is also not to be expected even if the design does not have a concave form, as the bottom part of the back is still stably positioned on the first raising plate 4.

FIGS. 3a and 3b depict the invented positioning aid 1 in the kyphosis position, in that the first raising pouch 6, the additional raising pouch 10 and the shoulder pillow 14 are inflated or filled with a fluid respectively. As can be discerned from the drawing, the shoulder pillow 14 mainly has a wedge-form in the longitudinal section at the vertical plane depicted in the Figure, whereby the point of the wedge points away from the head of the patient 2.

As a result of the inflation of the first raising pouch 6 by the first raising plate 4, a kyphosis position is created and the thorax of the patient 2 is raised diagonally upwards. In addition, due to the inflated additional raising pouch 10, the raising of the additional raising plate 8 raises ion the raising of the pelvis and the femur of the patient 2 is also diagonally raised upwards in the opposite direction. In doing so, it is essential that the pelvis and the adjoining lower part of the cervical column (=sacrum) are tilted forwards in a rotational manner as otherwise the movement is only applied to the joint between the femur and the pelvis.

With the assistance of the moveable slide 7 it is possible to individually adjust the relative position between the first raising plate 4 and the additional raising plate 8 to the size of the patient 2. The detection device 11 then externally displays the relative position. As soon as the correct position is reached, it can be locked in position using the fixing device 12.

A rough pre-adjustment of the position can already be carried out outside the tomograph when the patient 2 lies on the positioning aid 1. For this purpose the articulated axle 9 which should be positioned at the same height as an easily palpable point (=Trochanter major), should be visibly marked for the exterior. When used in the MR-tomography unit, a sensor tube containing signal-emitting material can be positioned exactly within this swivelling axis, the position of which being rendered discernible on a plain radiograph. The sensor tube which is not shown in the figure, must be positioned on an exactly defined position underneath the sacrum. Should this not be adhered to, one measures the distance between the sensor tube and a target point on the screen. A subsequence position correction can be carried out at all times without the patient 2 having to be removed from the tomograph and without any new plain radiographs having to be taken after the position has been amended accordingly.

The current position of the slide 7 can be read out on a display device. If one now requests the patient 2 to make a slight 'bridge', the locking position of the fixing device 12 can be loosened and the slide 7 moved by the required path length. Should this not be possible due to a lack of mobility of the patient 2 for example, the lordosis pillow 15 can be inflated until such time as the buttocks of the patient 2 are slightly raised, thereby releasing slide 7.

A lateral flexion is depicted in FIG. 4. For this purpose, a pelvic pillow 19 is positioned at the side of the centre axis of the base plate 3 at the same height as the pelvis of the patient 2, it being possible to fill this with fluid. On the same side on which the pelvic pillow 19 is situated, a padded deflection device 20 with a deflection rod 21 is situated at the foot-end of patient 2 at a distance from the centre-axis for the deflection of the feet of the patient 2, the said device being situated from the longitudinal direction of the base plate 3. The padding of the deflection device 20 can also be filled with a fluid.

However, the lateral flexion of the LVC is also only seldom used during a conventional myelograph (mainly with listheses). It would therefore certainly be tenable if a small amount of additional manual work would be required for the positioning of the patient in such cases. After the pelvic pillow 19 has been inflated, the deflection device 20 can be used to bring the straightened legs of the patient 2 by moving the deflection device 20 in the direction of the two double-arrows in FIG. 4, the deflection device 20 then being fixed in this position. It is also the case here that it can be adapted to the various patient sizes without any difficulty.

In FIG. 5, one can discern a swivelling reclining plate 23 which is situated next to the raising plate 4 which has been raised by means of the inflation of the raising pouch 6 around a horizontal articulated axle 22a which can be swivelled around the articulated axle 22a, this articulated axle running horizontally and transverse to the z-direction, the reclining plate 23 hooks into the hook-shaped recess 18 by means of the bolts 22. The raising plate 4 is linked to the reclining plate 23 using the pins 22. When the first raising plate 4 is raised or lowered, the reclining plate 23 is taken with it via the articulated axle 22a, whereby its end which faces away from the articulated axle 22a can be moved in the z-direction on a supporting surface 24.

In the position depicted in FIG. 5, a reclining of the CVC is achieved, whereby the head of the patient 2 being examined (not shown here) is inclined diagonally backwards, whereby the thorax is positioned diagonally upwards over the first raising plate 4.

Furthermore, an inclination rocker 25 is envisaged in FIG. 5, this having a recess 26, in which the reclining plate 23 is retained in the normal position depicted in FIG. 6.

The inclination rocker 25 is positioned on two lateral swivel fixed pivot brackets 27, 27' so that it can be swivelled. The swivel fixed pivot brackets are fixed laterally to the left and right of the head; the inclination rocker 25 swivelling around the swivelling axis 28 positioned to the left and right of the head, these being so positioned that they can be swivelled around a joint horizontal swivelling axis 28, whereby the swivelling axis 28 is positioned with a vertical clearance from the base plate 3. In addition, an inflatable raising pouch 29 which can normally be filled or inflated, is situated between the inclination rocker 25 and the base plate 3, which as depicted in FIG. 7 enables the inclination rocker 25 to be raised together with the reclining plate 23 retained by it, this resulting in a swivelling around the swivelling axis 28. When doing so, the pin 22, is removed from the hook-shaped recess 18 in an upwards direction, it subsequently being removed over the top-end of the device 1 in the direction of the head.

As is clear from FIG. 7, the reclining position originates from the first raising plate 4 in the horizontal normal position with the deflated first raising pouch 6.

The vertical clearance between the swivelling axis 28 of the inclination rocker 25 and the base plate 3 is so calculated that the turning of the head of the patient 2 being examined is mainly possible to the extent of its physiological axis of rotation.

The horizontal projection of the reclining plate 23 shown in FIG. 8a from the top shows an imaginary centre of motion 36, around which the lateral flexion movement takes place. In FIG. 8a, one can also discern the swivel fixed pivot brackets 37, 37' positioned on either side for the retention of the hinge pin 22.

FIG. 8a also depicts a curved guide rail 38, which connects both of the swivel fixed pivot brackets 37, 37', on which a slide ring 31 can be moved in the direction of the double-arrow along a vertical axis in the normal position. A cross-section of the guide rail 38 is depicted in a sagittal section of the vertical centre plane of the reclining plate 23 depicted in FIG. 8a, as shown in FIG. 8b.

Finally, FIG. 9 depicts a vertical section vertical to the z-axis which includes the swivelling axis 28 of the inclination rocker 25. A lateral flexion shell 30 which can rotate around the vertical axis 32 is supported by the slide ring 31 which is in turn positioned on the reclining plate 23. Where possible, this should correspond with the physiological axis of rotation of the head of the patient 2 being examined. The lateral flexion shell 30 of the design depicted in the drawing is of a hollow design and can include one or more surface coils in its cavity 35, or it can include the lower half of a coil system for the MRT, for example.

The lateral flexion shell 30 includes a length compensation shell 33, which can in the normal position, be moved linearly parallel to the z-direction. In turn, a rotation shell 34 is positioned within the length compensation shell 33 which can rotate and be fixed to, a horizontal axis in the normal position. This enables all possible movements of the human head to be defined, reproduced and held in position.

The invention claimed is:

1. A positioning aid (1) for the tomographic functional examination of vertebrates, especially humans, with a base plate (3) which extends along a z-direction parallel to the tomograph axis, the said plate being preferably interlocked with a mobile trolley, whereby a shoulder-plate is fitted to the base plate (3), in the same position as the thorax of the patient (2) who is being examined, enabling the position of the thorax of the patient (2) being examined to be continuously raised in the direction of the head when seen in comparison with the position of the base plate, a swivelling reclining plate (23) being linked to an articulated axle (22a) which runs horizontally in a direction transverse to the z-direction being linked via an articulated axle, it being possible to lower the said plate (23) in the direction of the base plate (3)
characterised in that:
the shoulder plate is firstly designed in the form of a raising plate (4), the end of which is linked to the base plate (3) facing away from the head, this being swiveled via an articulated axle (5) which is parallel to the articulated axle (22a) of the reclining plate (23), and in that a first raising pouch (6) of an elastic material is situated between the base plate (3) and the first raising plate (4), which when filled with a fluid raises the first plate (4) from the base plate (3) from one side, in that when the raising plate (4) is raised or lowered, the reclining plate (23) moves with it via the articulated axle (22a), whereby it is movable in a z-direction at the end which faces away from the articulated axle (22a), it preferably being positioned on a support surface (24) in such a way that it is displaceable.

2. Device according to claim 1, characterised in that an inclination rocker (25) is fitted at the same height as the head of the examined patient (2), the said rocker (25) having a recess (26) in which the reclining plate (23) is retained in the normal position, the inclination rocker (25) having two swivel fixed pivot brackets (27, 27') positioned laterally to the left and right of the head end, it being possible to swivel the inclination rocker (25) around a joint horizontal swiveling axis (28) which is vertical to the z-axis whereby the swivelling axis (28) is positioned with vertical clearance from the base plate (3), it also being intended that a raising pouch (29) which can be filled with a fluid and preferably inflated, be positioned between the base plate (3) and the inclination rocker (25).

3. Device according to claim 2, characterised in that the clearance between the swivelling axis (28) of the inclination rocker (25) and the base plate (3) is such that it is possible to rotate the head of the patient (2) being examined around its physiological axis of rotation.

4. Device according to claims 2 characterised in that the linking of the reclining plate (23) to the first raising plate (4) in so designed that when the inclination rocker (25) is activated, the reclining plate (23) is released from the first raising plate (4).

5. Device according to claim 4 characterised in that the coupling of the reclining plate (23) to the first raising plate (4) is realised in that the reclining plate (23) is linked by means of the pins (22) in the reclining plate, in that it hooks into a hook-shaped recess (18) in the first raising plate (4) which should preferably face upwards.

6. Device according to claim 1 characterised in that a lateral flexion shell (30) is positioned in the area of the head of the patient (2) being examined, this being connected to the reclining plate (23) via a slide ring (31), whereby the vertical axis (32) normally corresponds with the physiological axis of rotation of the head of the patient (2) being examined.

7. Device according to claim 6 characterised in that a length compensation shell (33) is positioned in the lateral flexion shell (30) and that the length compensation shell (33) moves linearly in a direction parallel to the z-direction.

8. Device according to claim 7 characterised in that a rotation shell (34) is situated in the length compensation shell (33) which can be rotated around a horizontal axis which is situated parallel to the z-direction in the normal position, it also being able to fix it in position.

9. Device according to claim 6 characterised in that the tomograph is a magnetic resonance unit and that one or more surface coils are installed in the cavity (35) of the lateral flexion shell (30).

10. Device according to claim 6 characterised in that the tomograph is a magnetic resonance unit and that the lower half of a surface coil system is situated in the cavity (35) of the lateral flexion shell (30), the corresponding top half being situated outside the cavity (35).

11. Device according to claim 1 characterised in that an additional raising plate (8) is situated at the foot, the said plate being linked to a moving slide (7) which moves in a longitudinal linear direction, the articulated axle (9) of the plate running parallel to the articulated axle (5) of the first raising plate (4), whereby an additional raising pouch (10) filled with a fluid and preferably inflatable, is situated between the slide (7) and the additional raising plate (8), a device for the detection of the position of the slide 7 in relation to the first raising plate (4) is envisaged, it being possible to lock the slide (7) in a determinable position in relation to the first raising plate (4).

12. Device according to claim 1 characterized in that a shoulder pillow (14) is positioned on the first raising plate (4) in order to support the shoulder of the patient (2) being examined.

13. Device according to claim 12 characterized in that the shoulder pillow (14) is wedge-shaped in the longitudinal section at a vertical level included in the z-axis, whereby the point of the wedge points away from the head of the device (1).

14. Device according to claim 1 characterized in that a lordosis pillow (15), which has a concave upper surface transverse to the z-direction, and which can be moved along the base plate (3) in a longitudinal direction, is situated between the first and additional raising plate (8), preferably on the base plate (3).

15. Device according to claim 1 characterized in that an extension plate (16) is rigidly positioned at the head-end of the first raising plate (4) in such a way that it can be removed, the said extension plate (16) supporting a head pillowing (17) for the support of the head of the patient (2) being examined.

16. Device according to claim 1 characterized in that a pelvic pillow (19) is positioned at the same height of the pelvis of the patient (2) being examined, to the side of the centre-axis of the base plate (3), and that a deflecting device (20) is fitted to the foot end of the patient (2) being examined on the same side at a distance from the centre-axis, the said device (20) being preferably cushioned, it especially being in the form of a deflecting rod (21) for the deflecting of the feet of the patient (2) being examined from the longitudinal direction of the base plate (3).

17. Device according to claim 11 characterized in that a display is situated outside the tomograph for the optical visualization of the position value determined by the device (11) for the position of the slide (7) relative to the first raising plate (4).

18. Device according to claim 17 characterized in that the device (11) for detecting the relative position of the slide (7) comprises a signal-emitting sensor, especially a magnetic resonance signal, this being positioned in the swiveling axis (9) of the additional raising plate (8).

19. Device according to claim 1 characterized in that all of the filing or emptying actions with regard to the raising pouches or other tubes of the device (1) and the protection against the movement of the position of the slide (7) relative to the fundraising plate (4) are activated outside the tomograph.

20. Device according to claim 1 characterized in that all of the actuators, drive and control units of the device are situated outside the tomograph, preferably in a separate room and that all drive units can be actively halted by the patient (2) is being examined.

* * * * *